United States Patent [19]
Morita

[11] Patent Number: 5,542,941
[45] Date of Patent: Aug. 6, 1996

[54] ABSORBENT ARTICLE HAVING ELASTICIZED SIDE FLAPS

[75] Inventor: Yasuko Morita, Kobe, Japan

[73] Assignee: The Procter & Gamble Company, Cincinnati, Ohio

[21] Appl. No.: 439,907

[22] Filed: May 12, 1995

Related U.S. Application Data

[63] Continuation of Ser. No. 208,102, Mar. 8, 1994, abandoned, which is a continuation of Ser. No. 984,071, Nov. 30, 1992, abandoned.

[30] Foreign Application Priority Data

Nov. 29, 1991 [JP] Japan .................................. 3-98947 U

[51] Int. Cl.⁶ ...................................................... A61F 13/15
[52] U.S. Cl. .................. 604/385.1; 604/387; 604/385.2
[58] Field of Search ............................... 604/385.1–391, 604/358

[56] References Cited

U.S. PATENT DOCUMENTS

| | | |
|---|---|---|
| 2,064,431 | 12/1936 | Jurgensen . |
| 3,575,174 | 4/1971 | Mogor . |
| 3,658,064 | 4/1972 | Pociluyko . |
| 3,860,003 | 1/1975 | Buell . |
| 4,184,498 | 1/1980 | Franco . |
| 4,490,148 | 12/1984 | Beckestrom . |
| 4,579,556 | 4/1986 | McFarland . |
| 4,597,761 | 7/1986 | Buell . |
| 4,655,759 | 4/1987 | Romans-Hess et al. . |
| 4,668,230 | 5/1987 | D'amico et al. . |
| 4,692,163 | 9/1987 | Widlund . |
| 4,701,177 | 10/1987 | Ellis et al. . |
| 4,758,240 | 7/1988 | Glassman . |
| 4,758,241 | 7/1988 | Papajohn . |
| 4,770,657 | 9/1988 | Ellis et al. . |
| 4,886,512 | 12/1989 | Damico et al. . |
| 4,908,026 | 3/1990 | Sukiennik et al. ...................... 604/378 |
| 4,911,701 | 3/1990 | Mavinkurve . |
| 4,940,462 | 7/1990 | Salerno . |
| 5,009,653 | 4/1991 | Osborn, III ............................. 604/378 |
| 5,032,121 | 7/1991 | Mokry . |
| 5,074,856 | 12/1991 | Coe et al. . |
| 5,234,422 | 8/1993 | Snelles et al. ........................ 604/385.2 |

FOREIGN PATENT DOCUMENTS

| | | |
|---|---|---|
| 0091412 | 10/1983 | European Pat. Off. . |
| 8902228 | 3/1989 | Japan . |
| 2142241 | 1/1985 | United Kingdom . |
| 2156681 | 10/1985 | United Kingdom . |
| 2168253 | 6/1986 | United Kingdom . |
| 2214057 | 8/1989 | United Kingdom . |
| 2233235 | 1/1991 | United Kingdom . |

*Primary Examiner*—Randall L. Green
*Assistant Examiner*—Robert Clarke
*Attorney, Agent, or Firm*—Steven W. Miller; E. Kelly Linman; Jacobus C. Rasser

[57] ABSTRACT

An absorbent article having a liquid permeable topsheet, a liquid impermeable backsheet and a liquid absorbent pad for absorbing a liquid exuded from the human body positioned there between, and having an elasticized side flap along each side edge of the absorbent article. The side flap has a loop member formed from either the topsheet or the backsheet, or an optional secondary non-woven sheet, which extends from and loops back toward said side edge of said absorbent pad, and an inserted member formed from a layer which extends from said side edge of said absorbent pad. An elastic material is affixed along a portion of the length of the inserted member, and a seal affixes the inserted member inside the loop member at its base end.

The absorbent sanitary article provides improved fit and leakage protection with better comfort.

22 Claims, 14 Drawing Sheets

ABSORBENT ARTICLE HAVING ELASTICIZED SIDE FLAPS

This now abandoned is a continuation of application Ser. No. 08/208,102, filed on Mar. 8, 1994 now abandoned which is a continuation of application Ser. No. 07/984,071, filed on Nov. 30, 1992, now abandoned.

FIELD OF THE INVENTION

This invention relates to a novel absorbent article, particularly to a sanitary article such as a sanitary napkin or an absorbing sheet. As used herein, the term "absorbent article" refers to devices which absorb and contain body exudates, and, more specifically, refers to devices which are placed against or in proximity to the body of the wearer to absorb and contain the various exudates discharged from the body.

BACKGROUND OF THE INVENTION

There is required for an absorbent article such as sanitary napkins or paper diapers a good and comfortable fit to the body, in addition to preventing exudates from leaking.

There has been conventionally proposed, for example, a curved sanitary napkin in which an elastic material in initial tension is arranged at the longitudinal edge of the napkin. If a sanitary napkin is formed into a curved shape by an elastic material, the body fit is enhanced, and an improvement in wearer's feeling of fit as well as the reduction of side leaking can be achieved. Such sanitary napkins are disclosed in U.S. Pat. Nos. 4,668,230, 4,701,177 and 4,770,657.

In the absorbent articles disclosed in the above-mentioned U.S. Patents, an elastic material is directly or indirectly bonded to the edge of a sheet surface which contacts with the body. A seal is provided which divides the elastic material arranged at this edge and an absorbent core positioned at the center. In this conventional constitution, a curved shape is provided to an absorbent article such as a sanitary napkin by wrinkling the surface sheet and the elastic material.

However, the above-mentioned conventional absorbent article has a problem that causes an uncomfortable feeling due to a deep wrinkle caused on the surface sheet of the edge and impairs comfortableness at the time of using the absorbent article in a curved shape, particularly when the surface sheet is a plastic material. Therefore, such sanitary napkins are not completely satisfactory, and there remains a need for improvement in fit, comfort, and containment by sanitary napkins and other absorbent articles.

The object of this invention is to provide an absorbent article which can enhance body fit in usage and can achieve can improvement in comfort and reduction of side leakage.

SUMMARY OF THE INVENTION

This invention provides an absorbent article comprising a wearer-facing, body-contacting liquid permeable topsheet, a garment-facing liquid impermeable backsheet, and a liquid absorbent pad there between for absorbing a liquid exuded from the human body, characterized by comprising an elasticized side flap along each side edge of said absorbent article, said side flap comprising:

a loop member having a base end with an opening positioned toward the side edge of the absorbent pad, a distal end, a garment-facing portion and a wearer-facing portion;

an inserted member which extends through said base end opening into said loop member, and having a distal end and a base end;

an elastic material affixed along a portion of the length of said inserted member outboard of said base end, wherein said elastic material is not affixed to said loop member; and a seal attaching said inserted member to said garment-facing and wearer-facing portions of said loop member at said respective base ends.

DETAILED DESCRIPTION OF THE INVENTION

Figure 1:
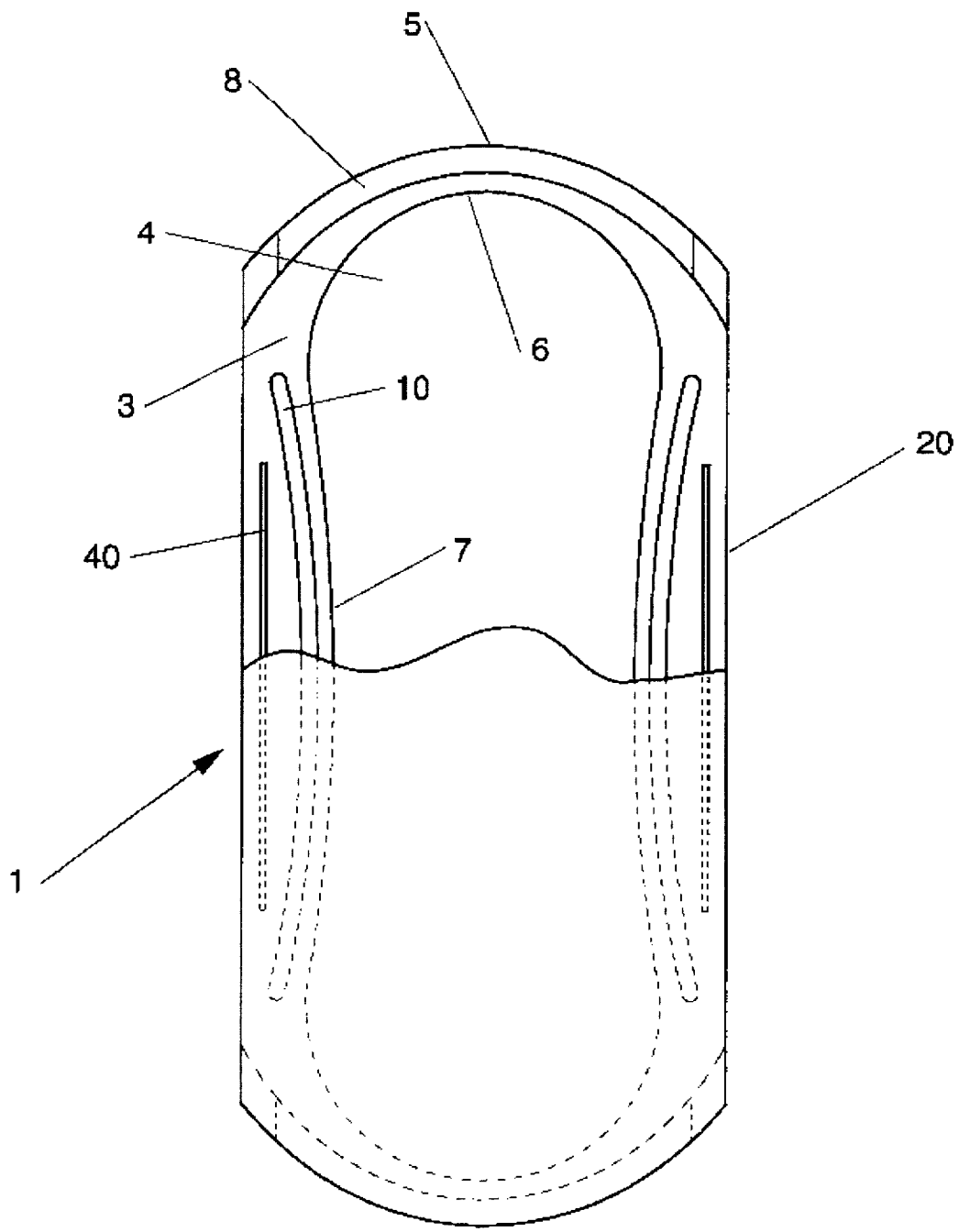
FIG. 1 shows a sanitary napkin of the present invention.

As shown in FIG. 1, the absorbent article 1 is usually substantially rectangular as a whole, though the end edges can be arc portions 5, respectively. The absorbent member 4 is generally smaller than the backsheet and is substantially rectangular, though both end edges are in the form of an arc portion 6 which pattern after the arc portion 5 of the backsheet 3, and both longitudinal sides 7 of the absorbent pad 4 are curved inward so that the center portion becomes slightly narrow.

Figure 2:
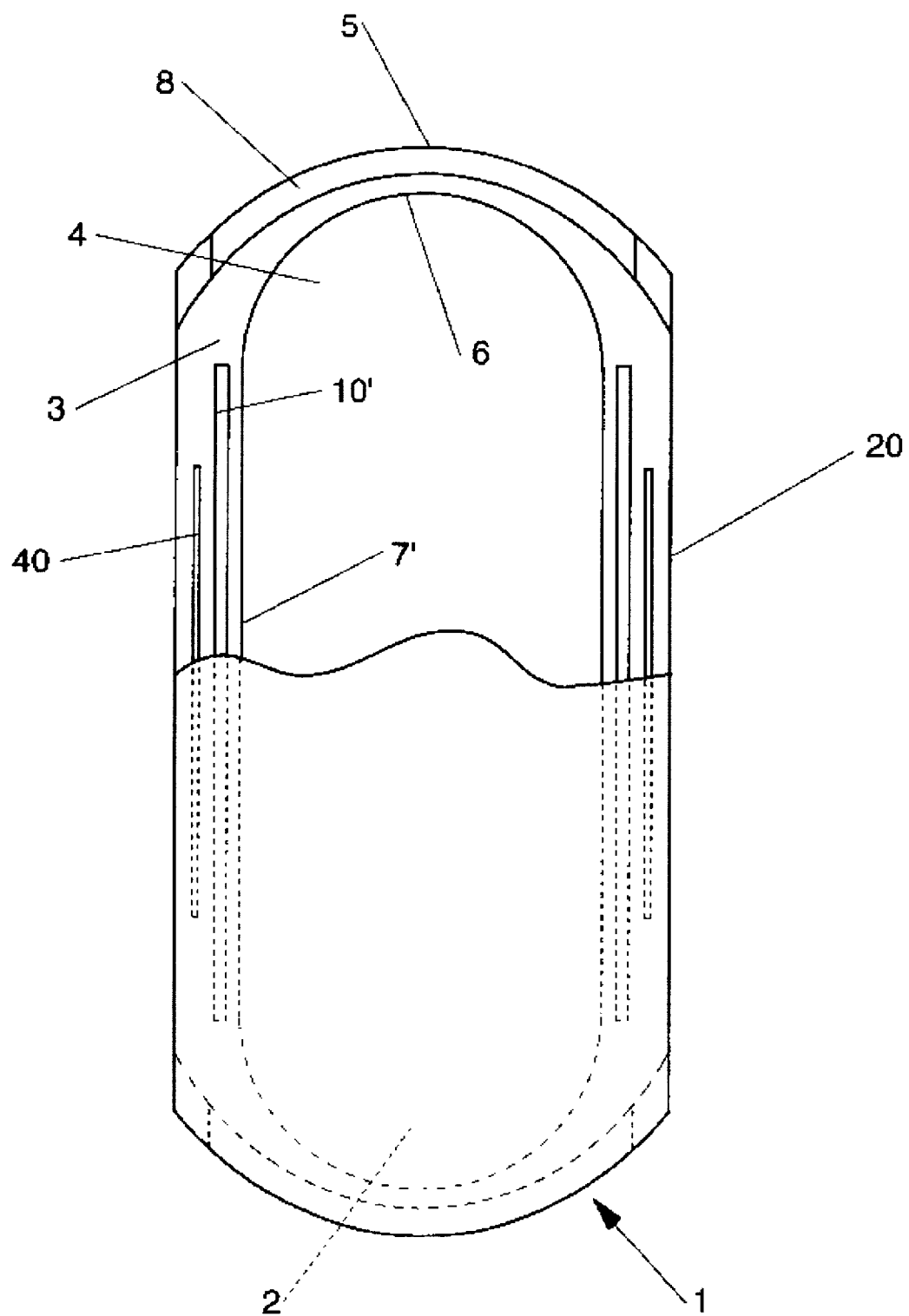
FIG. 2 shows an alternative sanitary napkin of the present invention.

FIG. 2 shows an example in which the longitudinal side 7' of an absorbent pad 4 and the heat seal 10' of the elasticized side flap 20 are formed as straight lines.

The absorbent article 1 has two centerlines: a longitudinal centerline and a transverse centerline. The term "longitudinal", as used herein, refers to a line, axis or direction in the plane of the absorbent article 1 that is generally aligned with (e.g., approximately parallel to) a vertical plane which bisects a standing wearer into left and right body halves when the absorbent article 1 is worn. The terms "transverse" or "lateral" as used herein, are interchangeable, and refer to a line, axis or direction which lies within the plane of the absorbent article 1 that is generally perpendicular to the longitudinal direction.

The topsheet is generally registered to cover completely the wearer-facing surface of the absorbent pad. Preferably, the topsheet extends beyond the periphery of the absorbent pad, or wraps around the lateral edges of the absorbent pad, and is secured to the backsheet to enclose the absorbent pad.

Figure 3:
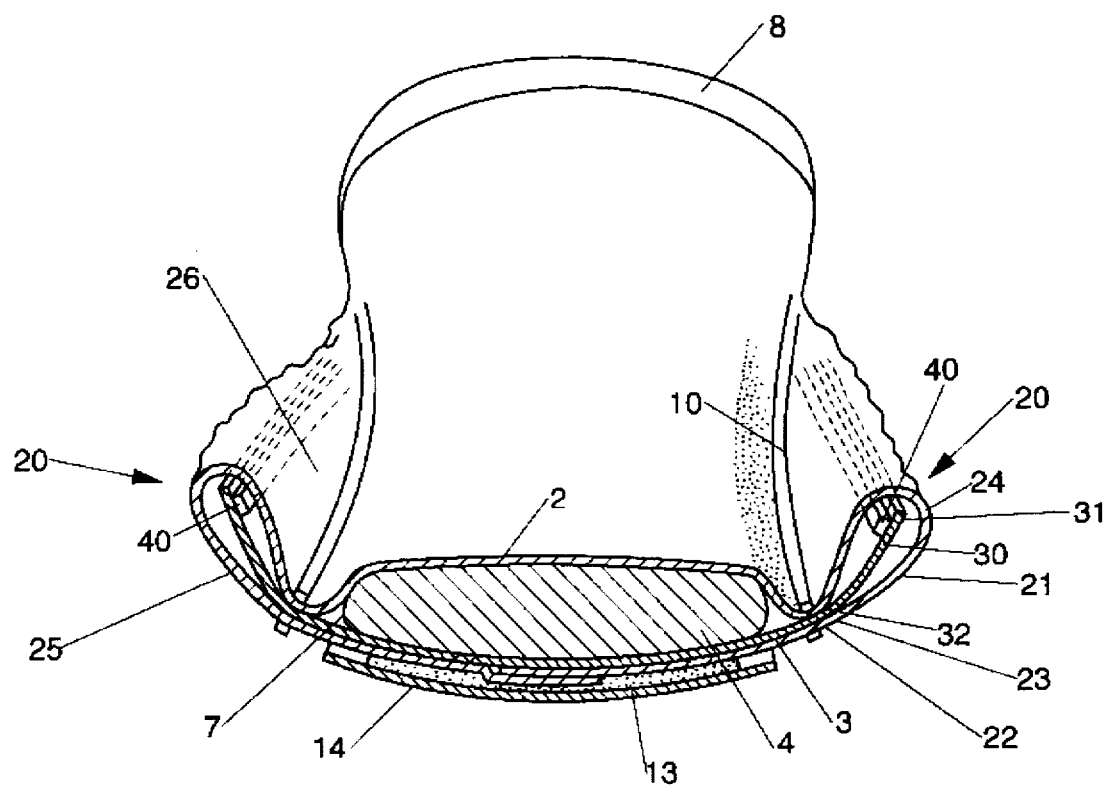
FIG. 3 shows a cross sectional view through a lateral centerline of a sanitary napkin of the present invention.

One embodiment of an absorbent article 1 according to this invention is shown in FIG. 3. The absorbent article 1 comprises a liquid permeable topsheet 2, a liquid impermeable backsheet 3, and a liquid absorbent pad 4 for absorbing a liquid exuded from the human body positioned there between and having a pair of side edges 7, characterized by comprising an elasticized side flap 20 along each side edge 7 of said absorbent pad, said side flap 20 comprising:

- a loop member 21 formed from a layer which extends from and loops back toward said side edge 7 of said absorbent pad and is selected from said topsheet 2 and said backsheet 3, said loop member 21 having a base end 22 with an opening 23 proximate said side edge 7 of said absorbent pad, a distal end 24, a garment-facing portion 25, and a wearer-facing portion 26;
- an inserted member 30 formed from a layer which extends from said side edge 7 of said absorbent pad and is selected from said backsheet and the topsheet, said inserted member 30 being inserted through said base end opening 23 into said loop member 21 and having a distal end 31 and a base end 32;
- an elastic material 40 affixed along a portion of the length of said inserted member 30 outboard of said base end 22 of said inserted member 30, wherein said elastic material is not affixed to said loop member 21; and
- a seal 10 attaching said inserted member 30 to said garment-facing portion 25 and wearer-facing portion 26 of said loop member 21 at said base end 22.

ELASTICIZED SIDE FLAPS

The elasticized side flap 20 is positioned along at least the central portion of each longitudinal side edge, usually symmetrically positioned about the lateral centerline of the article. The side flap 20 can extend to substantially the entire length of the longitudinal side edge of the article, though typically extends from 25%–100%, preferably 40%–60%, the length of the longitudinal side of the article. The elasticized side flap comprises a loop member, an inserted member, and elastic material, and a seal.

a. Loop member

The loop member 21 can be formed from either the topsheet 2 or the backsheet 3. Preferably, the loop member 21 is formed from the topsheet 2 which is more compatible with the skin. When the loop member 21 is formed from the topsheet 2, the backsheet 3 can serve as the inserted member 30. The loop member 21 is formed by extending the layer, in this case the topsheet 2, beyond the edge 7 of the absorbent pad and folding at a distal end 24 inward and back toward the edge of the absorbent core. By "inward" folding is meant folding toward a plane oriented in the x–y direction (or length and width) which passes through the middle of the z-direction (or height) of the absorbent core. When the topsheet (the wearer-facing layer) is the loop member layer, it is folded inward to the garment-facing direction; when the backsheet (the garment-facing layer) is the loop member layer, it is folded inward to the wearer-facing direction. As shown in FIG. 3, when the topsheet 2 forms the loop member 21, it can continue to extend and cover the backsheet-side of the absorbent article. The base end 22 of the loop member is proximate the side edge 7 and has an opening 23 through which the inserted member 30 can be inserted into the inside of the loop member 21. The width of the loop member 21 (from base end 22 to distal end 24) is generally from 10–25 mm, preferably about 15–20 mm. The base end 22 is positioned outboard the edge 7 of the absorbent pad, generally not more than 20 mm, preferably not more than 5 mm. Most preferably, the base end 22 is positioned as close to the absorbent pad edge 7 as possible, along the entire length of the side flap.

b. Inserted member

Figure 3A:
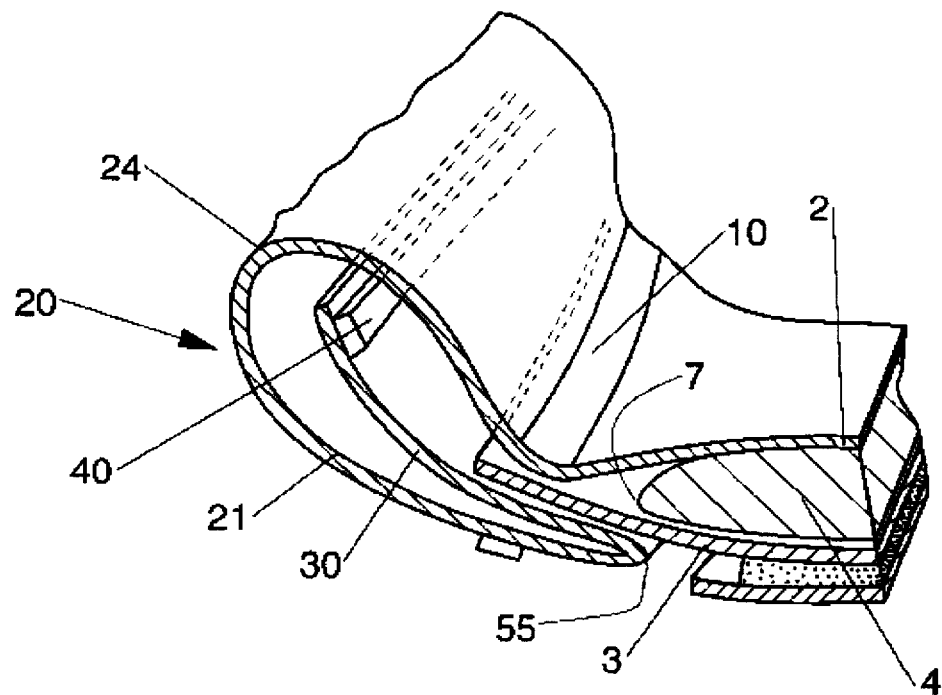
FIG. 3a shows a partial sectional view through a lateral centerline of another sanitary napkin of the present invention.
Figure 3B:
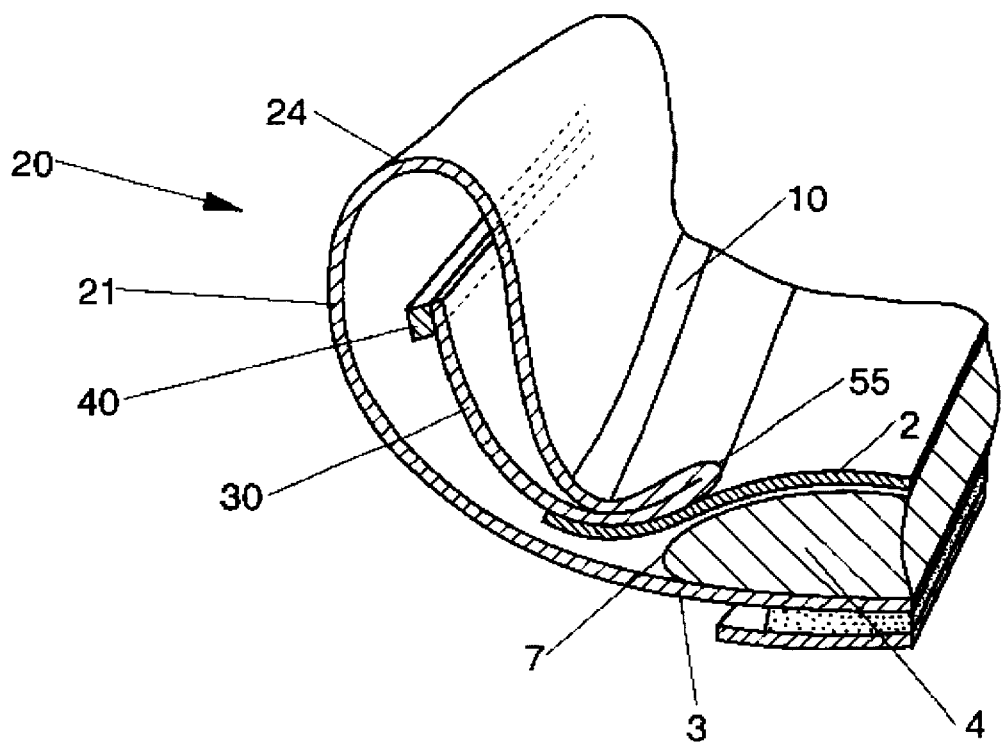
FIG. 3b shows a partial sectional view through a lateral centerline of still another sanitary napkin of the present invention.

The inserted member 30 is formed by extending the backsheet 3, or the topsheet 2 when the backsheet forms the loop member, beyond the edge 7 of the absorbent pad 4, through the opening 23 and into the loop member 21. The distal end 31 of the inserted member can extend to the distal end 24 of the loop member. It can also be folded or curled over inside the loop member 21. Preferably, the portion of the inserted member 30 extending beyond the base end 22 of the loop member has an effective length of at least 5 mm, more preferably about 10–15 mm. The distal end 31 of the inserted member 30 is intended to be free of and not attached to the loop member 21, at least along the center portion thereof. Alternatively, the topsheet or the backsheet can also serve as both the loop member and the inserted member. As shown in FIG. 3a, the topsheet 2 forms the loop member 21 as herein before described, and is then folded inward again at the fold 55 located at or near the edge 7 of the absorbent pad. The remaining end portion of the topsheet is then inserted into the loop member. In this embodiment, the edge of the backsheet can extend to and be secured by the side seal 10, and can optionally be inserted into the loop member as an inserted member. Conversely, as shown in FIG. 3b, the backsheet, though it is not as compatible with the skin of the wearer, can form both the loop member and the inserted member. In such cases, the seal 10 is made between the distal edge 24 and fold 55 of the folded backsheet 3.

c. Elastic member

The elastic material 40 provides the elasticity to the elasticized side flap. The elastic material 40 is affixed along at least a portion of the length of the inserted member 30 outboard of the base end 32. Generally, the elastic material 40 is pre-stretched prior to affixment by means 41 (not shown) to the inserted member 30. When the force used to hold the elastic material in the pre-stretched state is released, the elastic material contracts and tends to gather the inserted member. The seal 10 secures the inserted member 30 to the loop member 21 at its base end 32, and prevents the elastic material 40 from contracting completely to its fully relaxed position. Preferably, the elastic material 40 is affixed along at least 25% the length of the inserted member 30, more preferably along 40%–60% of the inserted member. The elastic member 40 is not attached to the loop member 21. Any stiffness or wrinkling formed in the inserted member 30 as a result of the contraction of the elastic member 40, or due to the elastic material 40 itself, is separated from the skin of the wearer by the loop member 21 layer, thus resulting in no reduction in comfort and skin friendliness. Because the elastic material does not come in direct contact with the skin of the wearer, a broad range of materials and elastic conditions can be used. The elastic material 40 can be elastic strings, strands, or films made from materials including: synthetic or natural rubber, such as LYCRA, elastomeric scrim, elastomeric films (including heat shrinkable elastomeric films), elastomeric woven or non-woven webs, elastomeric composites such as elastomeric non-woven laminates, synthetic or natural rubber foams, and the like. A preferred elastic string is a natural rubber commercially available under the designation 9411 produced by Fulflex, R.I. The elastic material can be pre-stretched to any length suitable to gather or contract the side flaps 20 to the desired shape, without causing significant adverse affect on the skin of the wearer. Generally, the elastic material can be pre-stretched from about 5% to 100% (105% to 200% of the original, relaxed length), more preferably from about 10% to about 30%. The elastic material can be affixed to the inserted member using an affixing means 41, such as a mechanical bond or adhesive bond. Mechanical bonds can include pressure or heat bonds that can bond the inserted member to the elastic. More preferably, an adhesive is used. A suitable adhesive is a hot-melt adhesive such as marketed by Findley Adhesives, Inc., Elm Grove, Wis., as Findley Adhesives H2085 or H2119. The inserted member 30 can be folded or curled around the elastic material 40 to improve the attachment. Alternatively, particularly when it is a stretchable film, the elastic material 40 can be wrapped around the distal end 31 of the inserted member 30. The elastic material 40 is preferably affixed at least about 5 mm from the base end 32 of the inserted member, more preferably about 10–15 mm from the base end. Positioning the elastic material 40 attachment away from the base end 32 of the inserted member provides the contracting elastic material with leverage to gather the distal end of the inserted member and to pull upward the ends of the absorbent article to conform the article to the shape of the wearer, and enables the elasticized side flaps to stand upward and press against the thighs of the wearer for better fit and leakage protection.

d. Seal

The seal 10 of the side flap 20 is made along the base end 22 of the loop member 21. The seal 10 can be continuous or intermittent; it can be a straight line or curvilinear. Preferably a curvilinear seal is one curved inward toward the absorbent pad and preferably having a curvature of up to 30 degrees. Preferably the seal (and the base end of the loop member) will conform with the shape of the side edge 7 of the absorbent pad. The length of the seal is generally at least as long as the elastic member; preferably it is longer than the elastic means. In a typical sanitary napkin of the present invention, the seal is from about 50–280 mm, more preferably from about 100–160 mm. in length. The seal serves to anchor the inserted member 30 and allows the elastic member 40 to pull up the longitudinal ends of the absorbent pad. The seal 10 also helps to prevent leakage from the side of the absorbent pad 4. The seal 10 can be a mechanical seal or an adhesive seal. The seal must be sufficient to bond together the garment-facing portion 25 and the wearer-facing portion 26 of the loop member 21 to the inserted member 30 at their respective base ends. The seal 10 can be a mechanical seal or an adhesive seal. Mechanical energy seals are preferred. As used herein, "mechanical energy" includes also thermal energy such as that employed in a heat seal. Such mechanical energy can be applied preferably in the form of an ultrasonic apparatus or pinch roller, which are well known for such purposes. A preferred mechanical seal is a pressure bond seal which bonds together the thermoplastic material of the loop member 21 to the thermoplastic material of the inserted member 30. In one suitable method of sealing the side flap, the assembled article is passed between a rotating anvil roll and a rotating pressure roll which typically exert about 1500–5000 kilograms force per square centimeter pressure on the sealing area, thereby forming a seal having a width generally from 0.5–6 mm, more preferably from 2–4 mm. Preferably, a temperature below about 80 degrees centigrade is used. It is most preferred to operate the anvil and the pressure roll at their ambient temperature. A higher temperature can be used so long as it is well below the thermoplastic melting temperature of the layers, to avoid damaging or weakening these materials at such temperatures. Another preferred method of forming the seal 40 is a heat seal made by heating the rotating anvil roll and/or the rotating pressure roll at or above the melting temperature of the thermoplastic materials of the elastic panels and chassis, and applying a considerably lower pressure to avoid excessive damage and weakening of the non-woven fabric layers in the area of the attachment lines. The seal can also be made by using an adhesive or chemical seal to bond the materials of the loop member 21 and the inserted member 30 together.

SECONDARY NON-WOVEN SHEET

Figure 4:
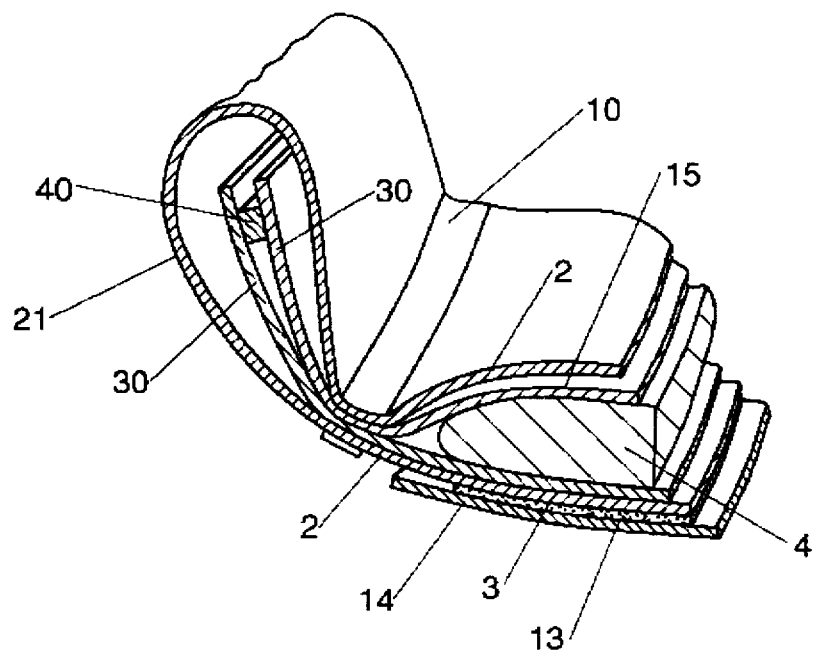
FIG. 4 shows a partial sectional view through a lateral centerline of yet another sanitary napkin of the present invention.
Figure 4A:
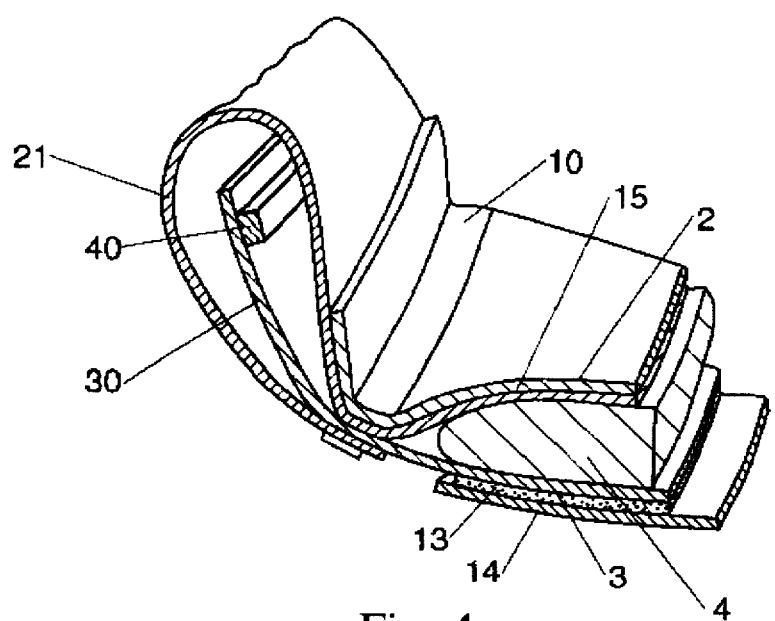
FIG. 4a shows a partial sectional view through a lateral centerline of still yet another sanitary napkin of the present invention.
Figure 4B:
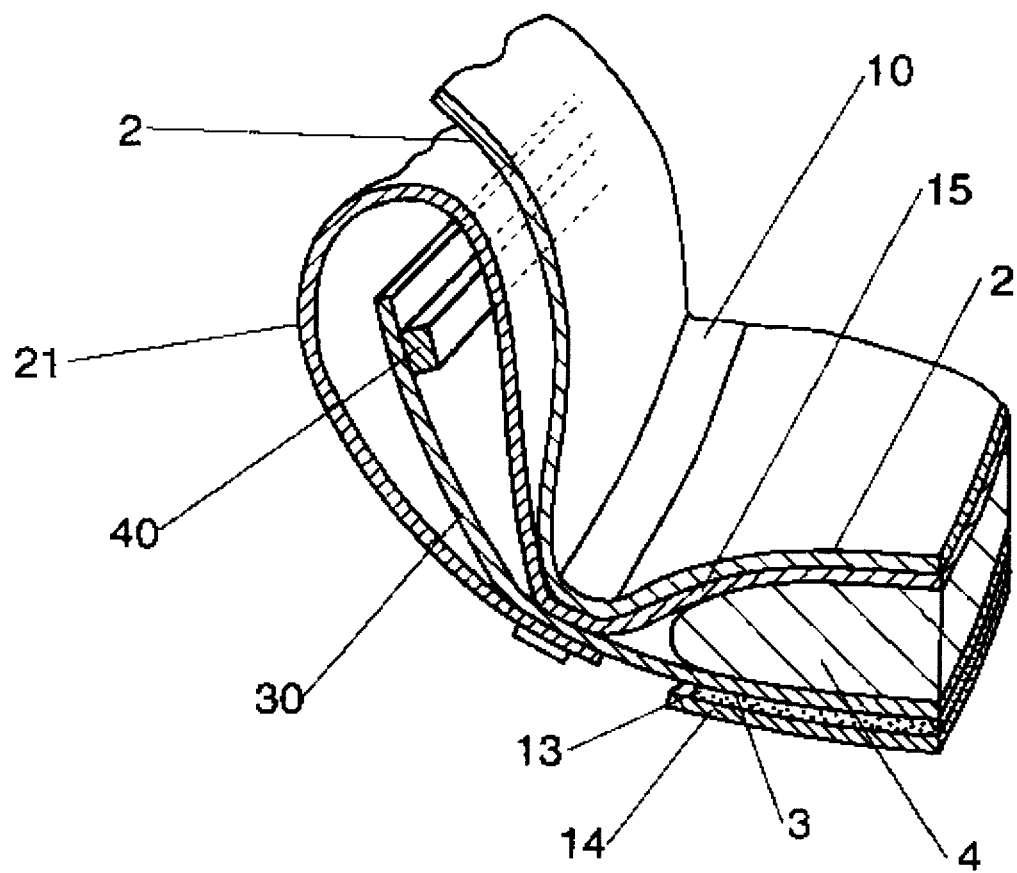
FIG. 4b shows a partial sectional view through a lateral centerline of another sanitary napkin of the present invention.

Another preferred sanitary napkin of the present invention is further provided with a secondary non-woven sheet 15 positioned between the topsheet 2 and the absorbent member 4 as a secondary topsheet. The lateral ends of the secondary non-woven sheet can extend beyond the lateral edges 7 of the absorbent pad, and can serve as either the loop member 21 or as an inserted member 30. In this sanitary napkin, the topsheet 2, backsheet 3, or the secondary non-woven sheet 15 can be the loop member 21 layer; or a combination of these layers can be brought together to form the loop member. Preferably a layer not used to form the loop member 21 is used as an inserted member 30. In FIG. 4, the loop member 21 is formed by the topsheet 2 and the inserted member 30 is formed by the secondary non-woven sheet 15 and the backsheet 3. The elastic material 40 is attached to both inserted members. Alternatively, the backsheet 3 only or the secondary non-woven sheet 15 only can be used as the inserted member 30. In FIG. 4a the loop member is formed by the secondary non-woven sheet 15, and the backsheet is extended to form the inserted member 30. The topsheet 2 extends to and is secured along its side edge by the side seal 10. Alternatively as shown in FIG. 4b, the side edges of the topsheet can extend beyond the side seal to at least partially cover the loop member 21.

In another embodiment, the loop member can be formed by the backsheet 3, and the secondary non-woven sheet can be extended to form the inserted member. As in the previous embodiments, the topsheet 2 can extend to and be secured along its side edge by the side seal 10, or can be further extended beyond side seal 10 to cover a portion of the wearer-facing portion 26 of the loop member. The topsheet can instead be inserted into the loop member as a second inserted member.

Figure 5:
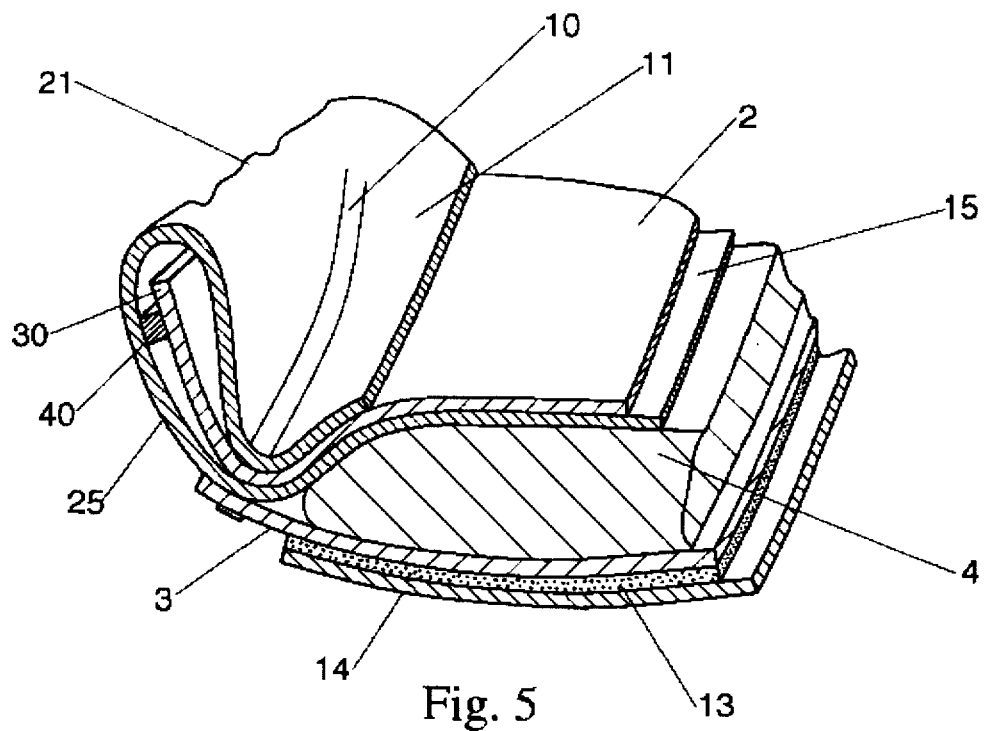
FIG. 5 shows a partial sectional view through a lateral centerline of yet another sanitary napkin of the present invention.
Figure 5A:
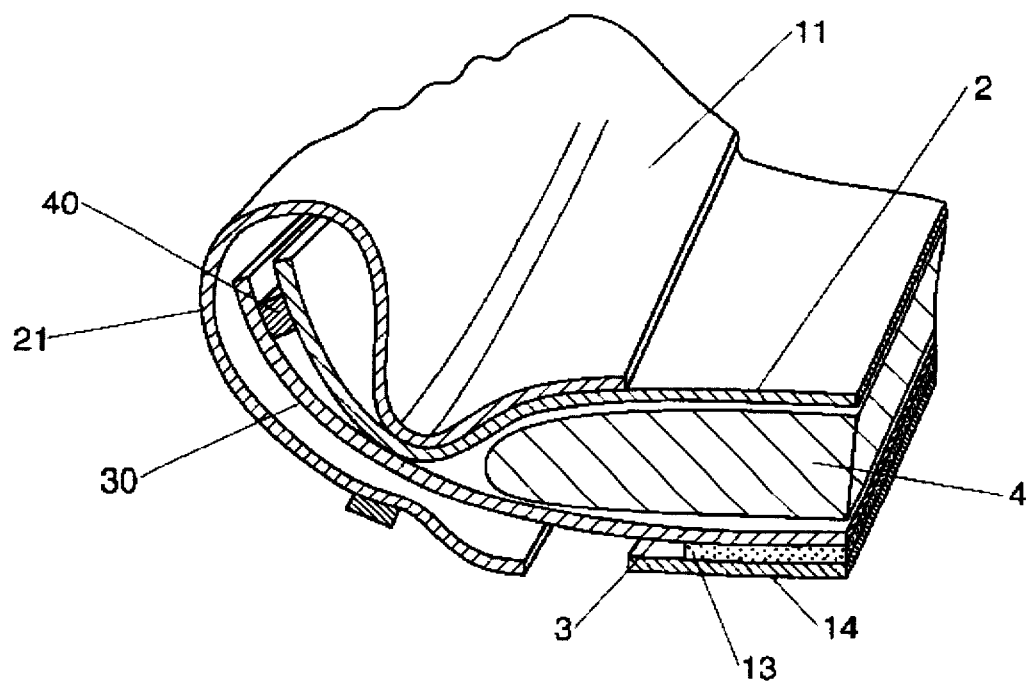
FIG. 5a shows a partial sectional view through a lateral centerline of still yet another sanitary napkin of the present invention.

In another sanitary napkin of the present invention, the absorbent article 1 has a topsheet 2 having a central portion and a side portion on each lateral side of the central portion, and a non-woven outer sheet 11 positioned on the wearer-facing surface along each side portion of said topsheet. The non-woven outer sheet 11 can be bonded, preferably with a mechanical seal (pressure or heat seal), continuously or in discrete areas, to the topsheet layer to secure its edges from rolling and tearing. The non-woven outer sheet 11 is preferably a soft, comfortable, skin-friendly non-woven fabric, which preferably forms the loop member 21 of the side flap. In this sanitary napkin, the topsheet 2, backsheet 3, or the non-woven outer sheet 11, or a combination of these, can form the loop member 21 layer. As shown in FIG. 5, the non-woven outer sheet 11 also loops back under the topsheet 2 to form the secondary non-woven sheet 15. The topsheet 2 forms the inserted member 30. The backsheet extends beyond the edge of the absorbent pad and is secured to the garment-facing surface 25 of the loop member by seal 10. In another preferred sanitary napkin shown in FIG. 5a, the non-woven outer sheet 11 forms the loop member 21 and then can extend to cover a portion of the garment-facing surface of the backsheet. In FIG. 5a, the backsheet 3 and the topsheet 2 form the inserted members 30; alternatively, the backsheet 3 and the topsheet 2 alone can form inserted member 30.

Figure 6:
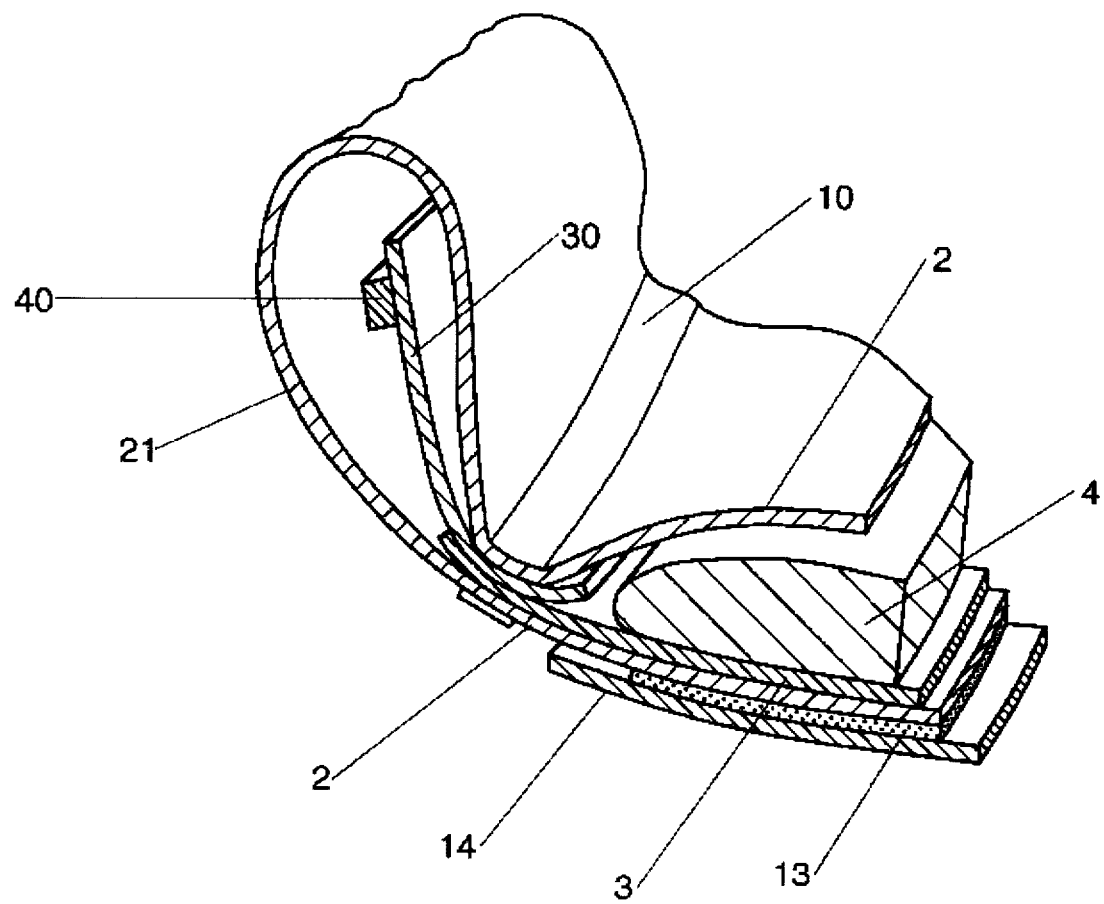
FIG. 6 shows a partial sectional view through a lateral centerline of an alternative sanitary napkin of the present invention.

FIG. 6 shows another sanitary napkin of the present invention where the inserted member 30 is a separate, distinct layer from any topsheet, backsheet, or other layer that can extend from the side edge 7 of the absorbent pad. In this embodiment, the elastic member can be integral with the inserted member, preferably with the elastic member positioned outboard of the base end 32 of the inserted member.

The use of the non-woven outer sheet 11 or the secondary non-woven sheet 15 to form the loop member reduces the amount of topsheet, which is typically a more expensive component, and hence reduces the production cost. Another benefit of the non-woven sheets is an improvement in comfort and skin friendliness.

The secondary non-woven sheet 15 and the non-woven outer sheet 11 preferably comprises a non-woven fabric for comfort and skin-feel. Non-woven webs can be made from natural fibers (e.g., wood or cotton fibers), synthetic fibers (e.g., polyester or polypropylene fibers), or a combination of natural and synthetic fibers. Preferably, the non-woven fabric is made of a hydrophilic or a surfactant-treated hydrophobic material. A preferred non-woven fabric is an air-through non woven supplied by Fukumura Seishi Kabushiki Kaisha. This non-woven comprises: a first layer which comprises about 50% w/w polyethylene (PE) and about 50% w/w polypropylene (PP) fibers having a denier of about 2, the fibers having a core made of polypropylene and a outer sheath surrounding the core made of polyethylene; and a second layer which comprises 50% w/w polyethylene (PE) and about 50% w/w polyester (PET) fibers having a denier of about 2, the fibers having a core made of polyester and a outer sheath surrounding the core made of polyethylene. The above fibers used in the first and second layers are known in the art as a "bi-component fiber". The sheet can be oriented with either layer facing the wearer.

ABSORBENT PAD

The absorbent pad 4 is any absorbent means which is capable of absorbing or retaining liquids (e.g., menses and/or urine). As discussed above, the absorbent core 4 can be manufactured in a wide variety of sizes and shapes (e.g., rectangular, oval, hourglass, dog bone, asymmetric, etc.) and from a wide variety of liquid-absorbent materials commonly used in absorbent napkins and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these. The configuration and construction of the absorbent core can also be varied (e.g., the absorbent core can have varying caliper zones (e.g., profiled so as to be thicker in the center), hydrophilic gradients, superabsorbent gradients, or lower density and lower average basis weight acquisition zones; or can comprise one or more layers or structures). The total absorbent capacity of the absorbent core should, however, be compatible with the design loading and the intended use of the absorbent article. Further, the size and absorbent capacity of the absorbent core can be varied to accommodate different uses such as incontinence pads, pantiliners, regular sanitary napkins, or overnight sanitary napkins.

Exemplary absorbent structures for use as the absorbent core of the present invention are described in U.S. Pat. No. 4,950,264 entitled "Thin, Flexible Sanitary Napkin" issued to Osborn on Aug. 21, 1990; U.S. Pat. No. 4,610,678 entitled "High-Density Absorbent Structures" issued to Weisman et al. on Sep. 9, 1986; U.S. Pat. No. 4,834,735 entitled "High Density Absorbent Members Having Lower Density and Lower Basis Weight Acquisition Zones", issued to Alemany et al. on May 30, 1989; and European Patent Application No. 0 198 683, The Procter & Gamble Company, published Oct. 22, 1986 in the name of Duenk, et al. Each of these patents are incorporated herein by reference.

In a preferred sanitary napkin of the present invention, an acquisition layer(s) can be positioned between the topsheet and the absorbent core. The acquisition layer can serve several functions including improving wicking of exudates over and into the absorbent core. There are several reasons why the improved wicking of exudates is important, including providing a more even distribution of the exudates throughout the absorbent core and allowing the sanitary napkin 1 to be made relatively thin. The wicking referred to herein can encompass the transportation of liquids in one, two or all directions (i.e, in the x-y plane and/or in the z-direction). The acquisition layer can be comprised of several different materials including non-woven or woven webs of synthetic fibers including polyester, polypropylene, or polyethylene; natural fibers including cotton or cellulose; blends of such fibers; or any equivalent materials or combinations of materials. Examples of sanitary napkins having an acquisition layer and a topsheet are more fully described in U.S. Pat. No. 4,950,264 issued to Osborn and U.S. patent application Ser. No. 07/810,774, "Absorbent Article Having Fused Layers", filed Dec. 17, 1991 in the names of Cree, et al. Each of these references are incorporated herein by reference. In a preferred embodiment, the acquisition layer can be joined with the topsheet by any of the conventional means for joining webs together, most preferably by fusion bonds as is more fully described in the above-referenced Cree application.

In another preferred sanitary napkin of the present invention, a wicking or fluid distribution strip (not shown) can be positioned between the topsheet and the absorbent core. The wicking strip provides permeability and diffusivity of the bodily liquids into and along the longitudinal length of the absorbent core. Preferred wicking strips are melt-blown or spun-bond non-wovens, and provide enhanced fluid distribution in the longitudinal direction of the absorbent article. A particularly preferred wicking strip comprises a series of longitudinally-oriented embossments or compressments, or both, in the non-woven wicking strip, as described in co-pending Japanese Patent Application No. 294665/1991, filed Nov. 11, 1991 (Procter & Gamble Far East Inc.). The longitudinal end edge portion 5 of the absorbent article 1 is typically formed by joining together the topsheet 2 and the backsheet 3, as well as any additional non-woven fabric layer 15, with a suitable seal 8, preferably a heat seal.

The backsheet 3 and topsheet 2, and any additional non-woven fabric layer 15 as applicable, can be secured to the absorbent core 4 by attachment means (not shown) such as those well known in the art. For example, the backsheet 3 and/or the topsheet 2 can be attached to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H2031. The attachment means will preferably comprise an open pattern network of filaments of adhesive as is disclosed in U.S. Pat. No. 4,573,986 entitled "Disposable Waste-Containment Garment", which issued to Minetola, et al. on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague, Jr. on Oct. 7, 1975 ; U.S. Pat. No. 4,785,996 issued to Zieker, et al. on Nov. 22, 1978; and U.S. Patent No. 4,842,666 issued to Werenicz on Jun. 27, 1989. Each of these patents are incorporated herein by reference. Alternatively, the attachment means can comprise heat bonds, pressure bonds, ultrasonic bonds, dynamic mechanical bonds, or any other suitable attachment means or combinations of these attachment means as are known in the art.

TOPSHEET

The topsheet 2 is compliant, soft feeling, and non-irritating to the wearer's skin, Further, the topsheet 2 is liquid pervious permitting liquids (e.g., menses and/or urine) to readily penetrate through its thickness. A suitable topsheet 2 can be manufactured from a wide range of materials such as woven and non-woven materials; polymeric materials such as apertured formed thermoplastic films, apertured plastic films, and hydroformed thermoplastic films; porous foams; reticulated foams; reticulated thermoplastic films; and thermoplastic scrims. Suitable woven and non-woven materials can be comprised of natural fibers (e.g., wood or cotton fibers), synthetic fibers (e.g., polymeric fibers such as polyester, polypropylene, or polyethylene fibers) or from a combination of natural and synthetic fibers. A preferred topsheet comprises an apertured formed film. Apertured formed films are preferred for the topsheet because they are pervious to body exudates and yet non-absorbent and have a reduced tendency to allow liquids to pass back through and re-wet the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel. et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr et al. on Jul. 31, 1984; and U.S. Pat. No. 5,006,394 "Multilayer Polymeric Film" issued to Baird on Apr. 9, 1991. Each of these patents are incorporated herein by reference. The preferred topsheet for the present invention is the formed film described in one or more of the above patents and marketed on sanitary napkins by The Procter & Gamble Company of Cincinnati, OH as "DRI-WEAVE".

In a preferred embodiment of the present invention, the body surface of the formed film topsheet is hydrophilic so as to help liquid to transfer through the topsheet faster than if the body surface was not hydrophilic so as to diminish the likelihood that menstrual fluid will flow off the topsheet rather than flowing into and being absorbed by the absorbent core. In a preferred embodiment, surfactant is incorporated into the polymeric materials of the formed film topsheet such as is described in U.S. patent application Ser. No. 07/794,745, "Absorbent Article Having A Nonwoven and Apertured Film Coversheet" filed on Nov. 19, 1991 by Aziz, et al., which is incorporated herein by reference. Alternatively, the body surface of the topsheet can be made hydrophilic by treating it with a surfactant such as is described in the above referenced U.S. Pat. No. 4,950,254 issued to Osborn, incorporated herein by reference.

BACKSHEET

The backsheet 3 is impervious to liquids (e.g., menses and/or urine) and is preferably manufactured from a thin plastic film, although other flexible liquid impervious materials can also be used. As used herein, the term "flexible" refers to materials which are compliant and will readily conform to the general shape and contours of the human body. The backsheet 3 prevents the exudates absorbed and contained in the absorbent core 4 from wetting articles which contact the sanitary napkin such as pants, pajamas and undergarments. The backsheet 3 can thus comprise a woven or non-woven material, polymeric films such as thermoplastic films of polyethylene or polypropylene, or composite materials such as a film-coated non-woven material. Preferably, the backsheet is a polyethylene film having a thickness of from about 0.012 mm (0.5 mil) to about 0.051 mm (2.0 mils). Exemplary polyethylene films are manufactured by Clopay Corporation of Cincinnati, OH, under the designation P18-0401 and by Ethyl Corporation, Visqueen Division, of Terre Haute, Ind, under the designation XP-39385. The backsheet is preferably embossed and/or matte finished to provide a more cloth-like appearance. Further, the backsheet 3 can permit vapors to escape from the absorbent core 4 (i.e., breathable) while still preventing exudates from passing through the backsheet 3.

In use, the sanitary napkin 1 can be held in place by any support means or attachment means (not shown) well-known for such purposes. Preferably, the sanitary napkin is placed in the user's undergarment or panty and secured thereto by a fastener such as an adhesive 13. The adhesive 13 provides a means for securing the sanitary napkin in the crotch portion of the panty. Thus, a portion or all of the garment-facing surface of the absorbent article 1 is coated with adhesive. Any adhesive or glue used in the art for such purposes can be used for the adhesive herein, with pressure-sensitive adhesives being preferred. Suitable adhesives are Century A-305-1V manufactured by the Century Adhesives Corporation of Columbus, OH; and Instant Lock 34-2823 manufactured by the National Starch and Chemical Company of Bridgewater, NJ. Suitable adhesive fasteners are also described in U.S. Pat. No. 4,917,697. Before the sanitary napkin is placed in use, the pressure-sensitive adhesive is typically covered with a removable release liner 14 in order to keep the adhesive from drying out or adhering to a surface other than the crotch portion of the panty prior to use. Suitable release liners are also described in the above-referenced U.S. Patent No. 4,917,697. Any commercially available release liners commonly used for such purposes can be utilized herein. Non-limiting examples of suitable release liners are BL30MG-A Silox E1/0 and BL30MG-A Silox 4P/O both of which are manufactured by the Akrosil Corporation of Menasha, WI. The sanitary napkin 1 of the present invention is used by removing the release liner and thereafter placing the sanitary napkin in a panty so that the adhesive contacts the panty. The adhesive 13 assists in maintaining the sanitary napkin in its position within the panty during use.

WINGS

Figure 7:
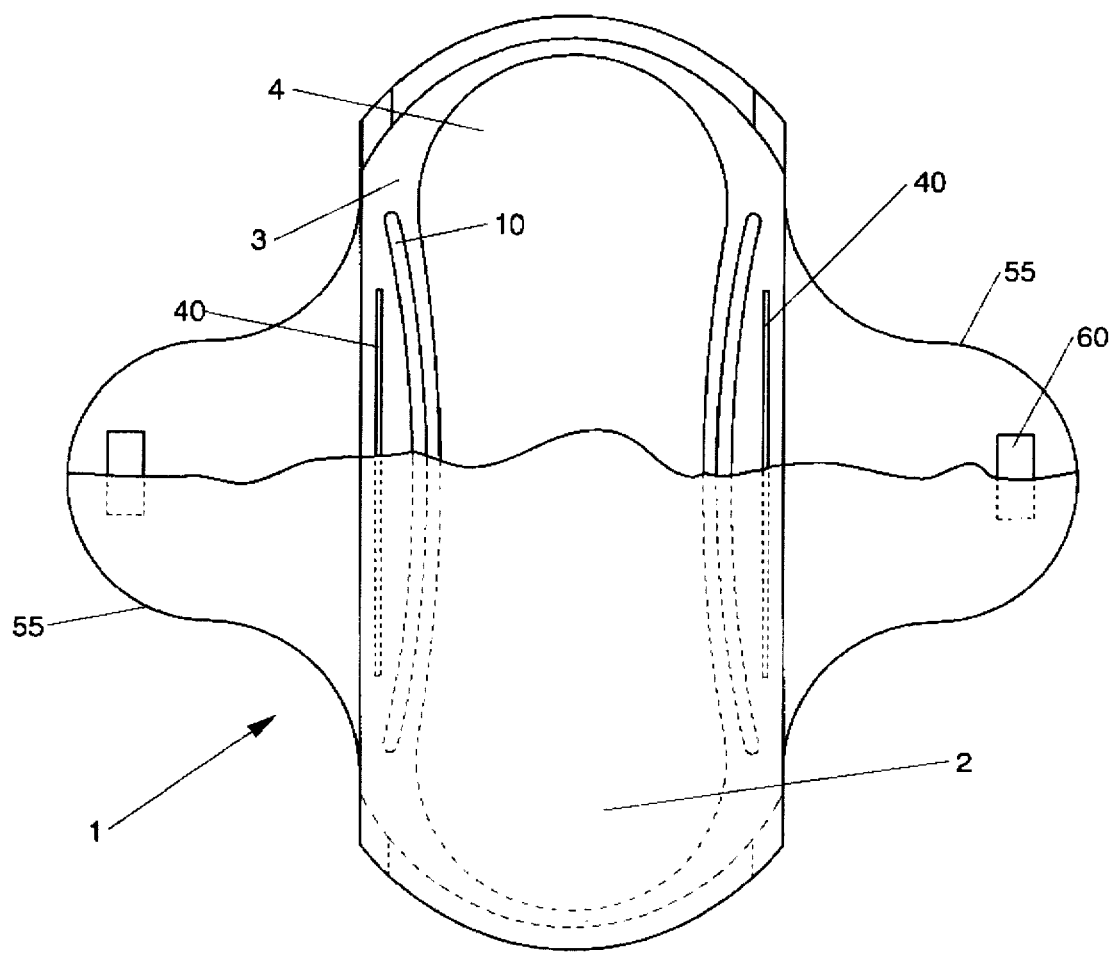
FIG. 7 shows another alternative sanitary napkin of the present invention further comprising a wing along each side edge.

A sanitary napkin of the present invention optionally has a wing or extending flap 50 which is adjacent to and extending laterally from a line of juncture 51 located along each side edge of the absorbent core. An example of such sanitary napkin of the present invention having wings is shown in FIG. 7. The wings 50 are configured to drape over the edges of the wearer's panties in the crotch region so that the wings 50 lo are disposed between the edges of the wearer's panties and the wearer's thighs. The wings 50 serve at least two purposes. First, the wings help to prevent soiling of the wearer's body and panty by menstrual fluid, preferably by forming a double wall barrier along the edges of the panty. In combination with the elasticized side flap, which also forms a barrier between the absorbent pad and the skin and panty of the wearer, the sanitary napkin of the present invention provides excellent protection against soiling of the wearer's body and panty. Second, the wings are preferably provided with attachment means 60 on their garment surface so that the wings can be folded back under the panty and attached to the garment facing side of the panty. Typically, attachment means 60 comprises a panty adhesive 61 and a release film 62 as described herein before. In this way, the wings serve to keep the sanitary napkin properly positioned in the panty.

The wings 50 can be constructed of various materials including materials similar to the topsheet 2, backsheet 3, or a laminate of these materials. Further, the wings can be a separate element attached to the main body of the napkin, or can comprise extensions of the topsheet 2 and backsheet 3 (i.e., unitary). A number of sanitary napkins having wings suitable or adaptable for use with the sanitary napkins of the present invention are disclosed in U.S. Pat. No. 4,687,478 entitled "Shaped Sanitary Napkin With Flaps", which issued to Van Tilburg on Aug. 18, 1987; U.S. Pat. No. 4,589,876 entitled "Sanitary Napkin", which issued to Van Tilburg on May 20, 1986; and U.S. Pat. No. 4,608,047, entitled "Sanitary Napkin Attachment Means", which issued to Mattingly on Aug. 26, 1986. Each of these patents are incorporated herein by reference.

It is most preferred that the attachment of the wing occur along line of juncture 51 which is inboard of (closer to the longitudinal centerline than) side seal 10. This enables the wing 50 and the side flap 20 to function independently.

The wing 50 can comprise one or more discrete fabric layers fastened or laminated together, for example by adhesive or mechanical bonding. For skin compatibility reasons, it is preferred that the wing comprise a non-woven or other material suitable for use as a topsheet on that surface which faces or contacts the skin of the wearer.

Figure 8A:
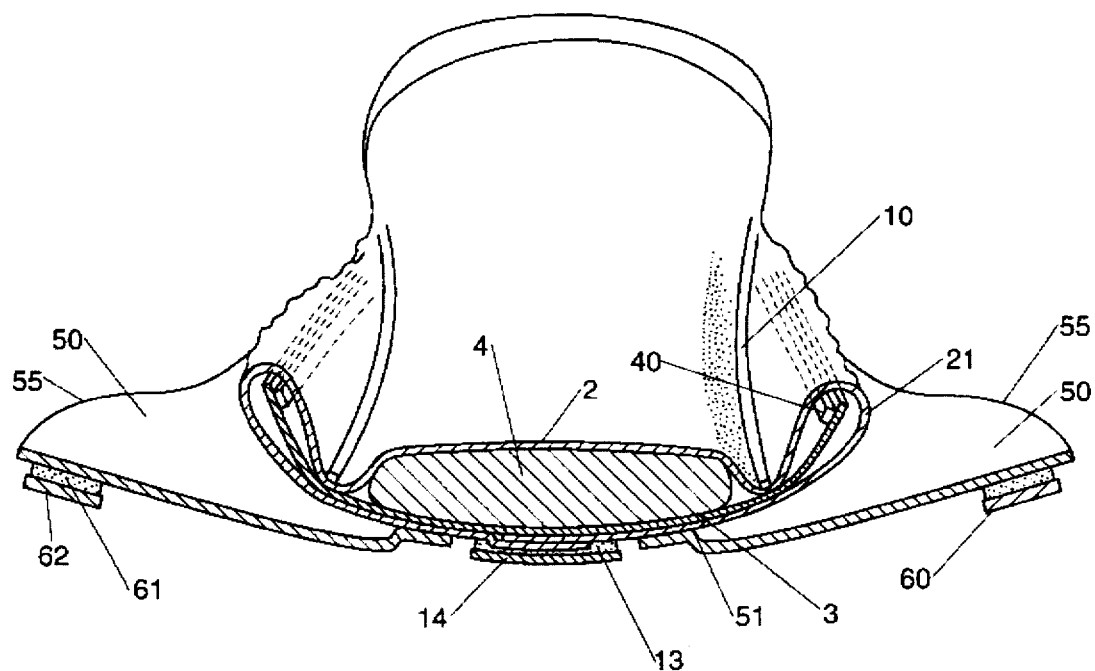
FIG. 8a shows a cross-sectional view through a lateral centerline of a sanitary napkin of the present invention further comprising a wing along each side edge.

FIG. 8a is a cross-sectional view of the sanitary napkin of FIG. 7. Each wing 50 is a separate member attached on the garment-facing side of the napkin. The wings 50 are preferably cut from a single web of material prior to attachment to the main body portion 8. As shown in FIG. 8c, the web of material 100 need only be as wide as the lateral width of one flap (or only slightly wider than the width of a flap). The edges of the web of material oriented in the machine direction can be trimmed to the desired curvature for the proximal edges of the flaps. After the edges are trimmed, the edges 55 of the flaps can be formed by cutting the web along a sinusoidal path. The sinusoidal cutting path can have an amplitude that extends from one edge of the web to the other. The sinusoidal cutting path forms flap pieces which are "nested" with each other. The cutting path can, thus, simultaneously form the edges of two different flaps.

Figure 8B:
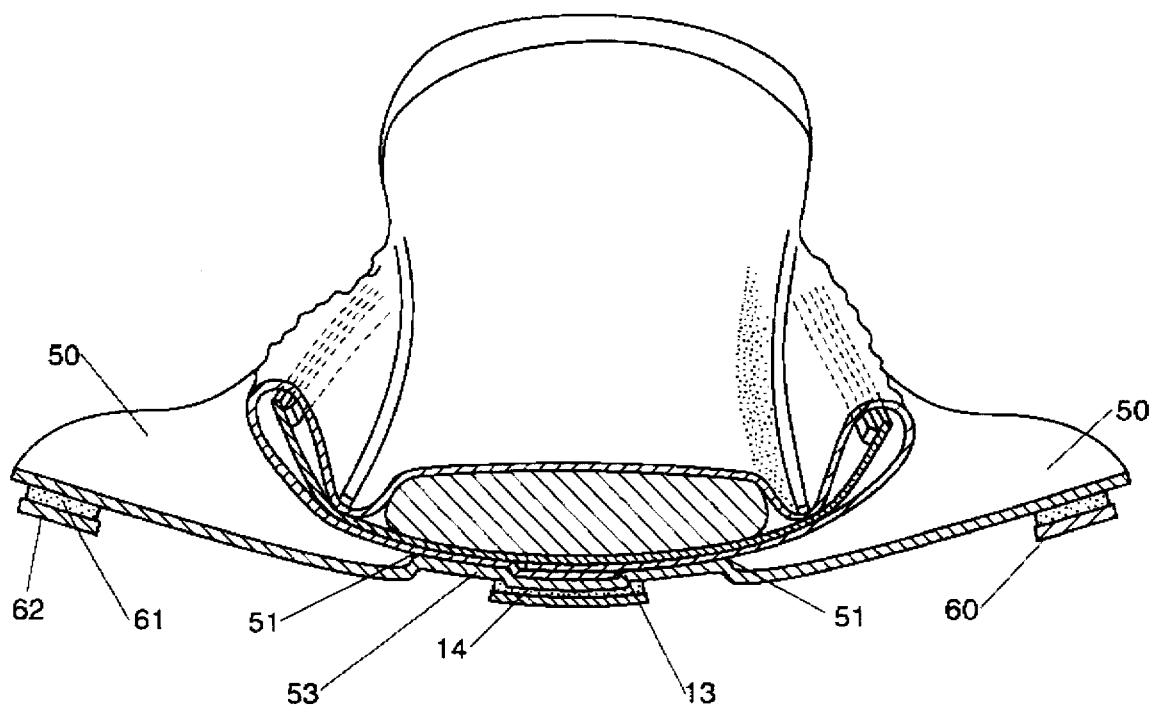
FIG. 8b shows a partial sectional view through a lateral centerline of yet another sanitary napkin of the present invention further comprising a wing along each side edge.
Figure 8C:
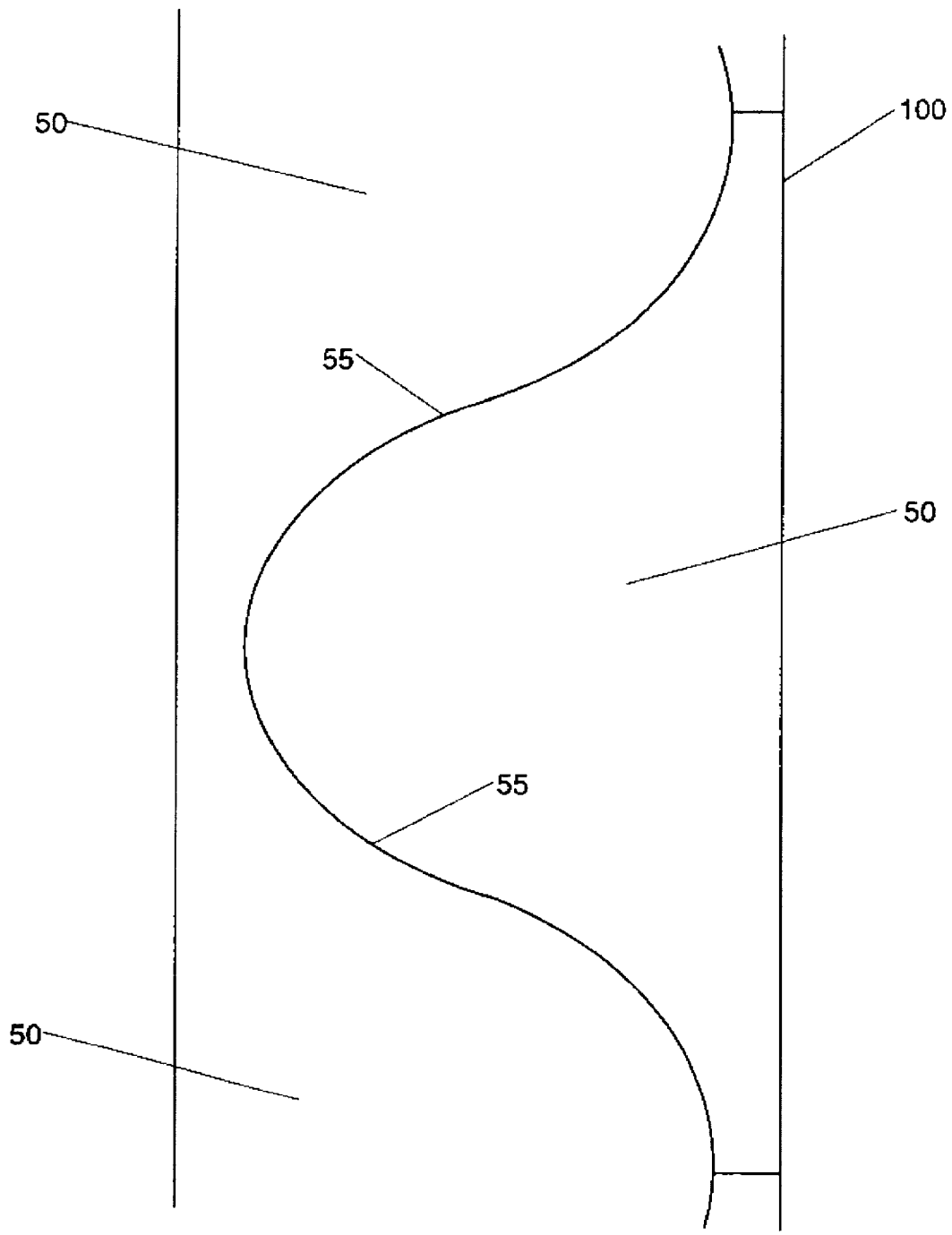
FIG. 8c shows a web of material used to form wings for use on a sanitary napkin of the present invention.

Alternatively, as shown in FIG. 8b, the two wings can be combined into a single wing member 53 which is attached to the garment-facing surface of the absorbent article using a mechanical or adhesive bonding as described herein before. The panty fastening adhesive 13 and release liner 14 are then affixed to the single wing member 53.

A preferred sanitary napkin extends the fabric layers used to form the elasticized side flap 20 to also form a portion of the wing 50. The loop member 21 and the inserted member 30 can continue to the garment-facing surface of the article to form wing 50. Since the topsheet, backsheet, secondary non-woven sheet and nonwoven outer sheet can form individually or in combination, either the loop member 21 or the inserted member 30, there are numerous possible embodiments of this sanitary napkin.

Figure 9A:
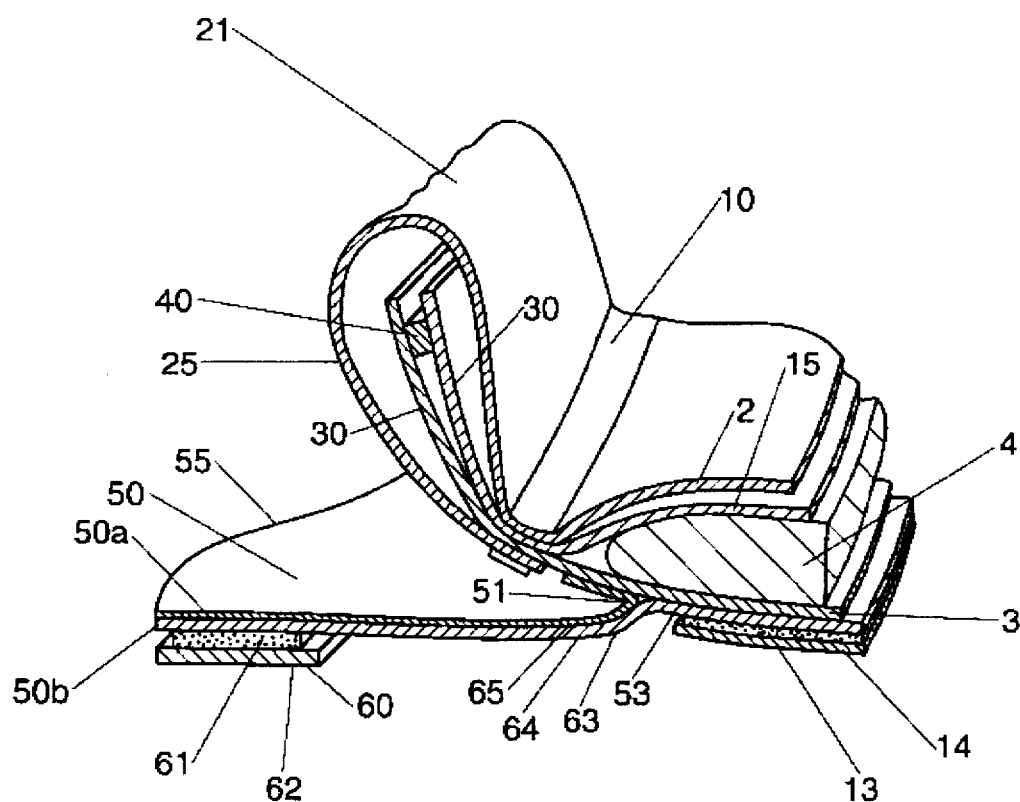
FIG. 9a shows a partial sectional view through a lateral centerline of still another sanitary napkin of the present invention further comprising a wing along each side.

In FIG. 9a, topsheet 2 extends beyond the edge of the absorbent pad to form the loop member 21. A secondary non-woven sheet 15 and the backsheet 3 form inserted members 30. The garment-facing portion 25 of the loop member extends beyond seal 10 and then folds outward again at fold 63 to form a folded portion 64. The layers of the folded portion 64 outboard of fold 63 are attached together with seal 65 using a mechanical or adhesive bond, forming line of juncture 51. Preferably the line of juncture 51 is formed inboard of side seal 10. The folded portion 64 extends beyond the line of juncture 51 to form the wing portion 50a of the wing 50. A second wing material 53 is laminated to the topsheet-formed wing portion 50a and to the garment-facing portion of the absorbent article, and forms wing portion 50 b.

Figure 9B:
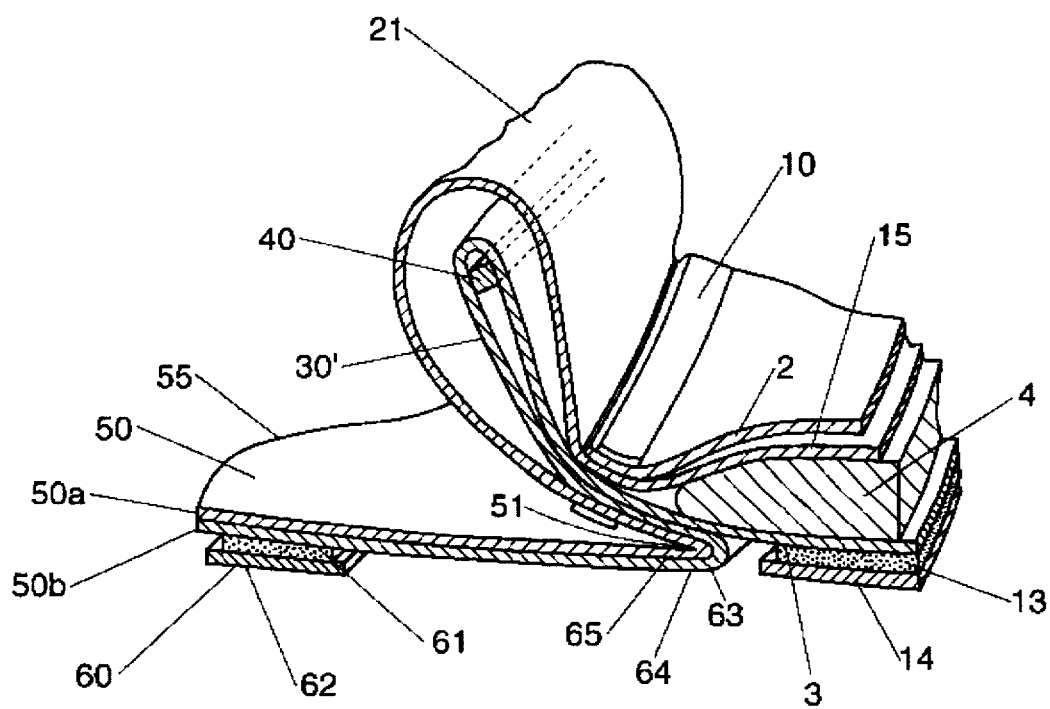
FIG. 9b shows a partial sectional view through a lateral centerline of yet another sanitary napkin of the present invention further comprising a wing along each side.

In FIG. 9b, secondary non-woven layer 15 forms loop member 21. The garment-facing portion 25 of loop member 21 then extends back beyond seal 10. Backsheet 3 extends beyond the edge of the absorbent pad and folds outwardly to form an inserted member loop 30'. The distal end of the inserted member loop 30' is inserted into loop member 21, and elastic 40 is attached inside the inserted member loop 30'. The garment-facing portion of the inserted member loop 30' extends beyond seal 10. The garment-facing portions of the inserted member loop 30' and the loop member 21 then fold outward again at fold 63 to form a folded portion 64. Seal 65 secures the layers of the folded portion 64 outboard of fold 63, forming the line of juncture 51. The folded portion 64 extends beyond the line of juncture 51 to form wing 50.

Figure 9C:
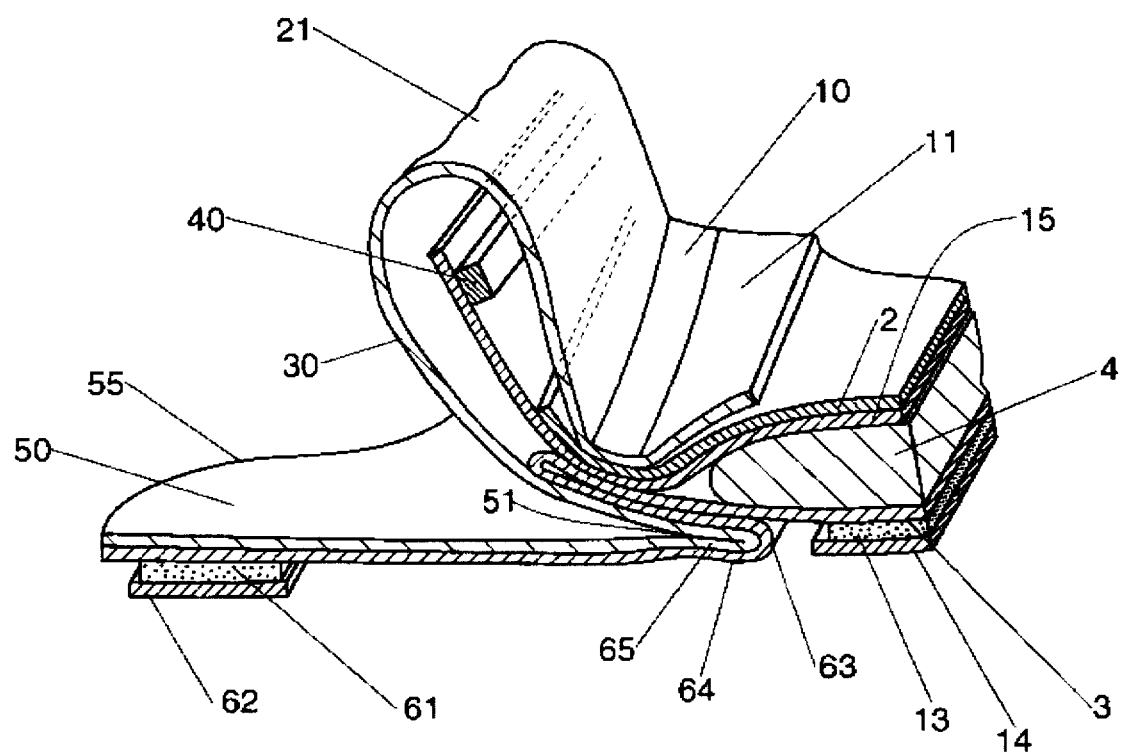
FIG. 9c shows a partial sectional view through a lateral centerline of still another sanitary napkin of the present invention further comprising a wing along each side.

Another preferred sanitary napkin is shown in FIGS. 9c. Non-woven outer sheet 11 forms loop member 21. The garment-facing surface of loop member 21 then extends beyond seal 10. Secondary non-woven layer 15 forms inserted member 30. Topsheet 2 is secured along its longitudinal edge by seal 10. Backsheet 3 extends beyond the edge of the absorbent pad and folds outwardly, at or just beyond side seal 10, back toward the center of the article. The extended backsheet layer and the garment-facing portion of the loop member 21 then fold outward again at fold 63 to form a folded portion 64. Seal 65 secures the layers of the folded portion 64 outboard of fold 63, forming the line of juncture 51. The folded portion 64 extends beyond the line of juncture 51 to form wing 50.

The wing 50 of the sanitary napkin can have zones of differential extensibility (not shown) for relieving the stresses that develop in the wings when the wings are folded down along the edges of the wearer's panties in the crotch. The wings are divided into a front half and a back half by a wing transverse centerline. The absorbent article has two corner regions (not shown) located adjacent the area of the ends of the junctures 51. One corner region is located adjacent the area of the juncture in each direction remote from the principal transverse centerline. The sanitary napkin comprises zones of differential extensibility which allow the corner regions to extend transversely outward to a greater degree than the portions of the sanitary napkin located along the wing transverse centerline. The zones of differential extensibility provide a means for the relief of stresses in the wings of the sanitary napkin when the sanitary napkin is placed in the wearer's undergarments. The zone of differential extensibility can be provided by a number of means, including stretching of the material, by pleating or folding of the fabric, or joined along a curved juncture. Preferably the line of juncture is curved inward toward the principle longitudinal centerline, whereby excess flap material is present in the corner regions when the wings is folded outward. Sanitary napkins comprising such zones of differential extensibility are disclosed in U.S. patent application Ser. No. 07/769891, Lavash et al., entitled "Absorbent Article Having Flaps and Zones of Differential Extensibility", filed Oct. 1, 1991.

As clearly seen from the above illustration, according to this invention, a sanitary napkin is provided comprising a loop member which stands up and helps the article to form a curved shape, thereby improving fit, comfort, and reducing the risk of side leakage. The elastic material is attached to the inserted member but is not attached directly to the loop member. Any stiffness or wrinkling formed in the inserted member as a result of the contraction of the elastic member, or due to the elastic member itself, is separated from the skin of the wearer by the loop member layer, thus resulting in no reduction in comfort and skin friendliness. Because the elastic material does not come in direct contact with the skin of the wearer, a broad range of materials and elastic conditions can be used.

While particular embodiments of the present invention have been illustrated and described, it would be obvious to those skilled in the art that various other changes and modifications can be made without departing from the spirit and scope of the invention. Therefore the appended claims are intended to cover all such changes and modifications that are within the scope of this invention.

I claim:

1. A sanitary napkin for placement in a user's panty, the sanitary napkin comprising:
    a main body portion comprising:
        a liquid permeable topsheet;
        a liquid impermeable backsheet joined with said topsheet;
        an absorbent pad for absorbing liquids positioned between said topsheet and said backsheet, said absorbent pad having a pair of side edges; and
        an elasticized side flap extending laterally outwardly from and along each said side edge of said absorbent pad, each said side flap comprising a member having a base end and a distal end extending laterally outwardly from said base end and an elastic material affixed along a portion of the length of said member laterally outboard of said base end; and
    a pair of wings attached to said main body portion and configured to be positioned over the edge of the user's panty.
2. The sanitary napkin of claim 1 wherein each said wing extends laterally outwardly beyond said distal end of said member so that said wing is folded back over the edge of the user's panty.
3. The sanitary napkin of claim 2 wherein said wings are configured to form a double-wall barrier along the edge of the panty.
4. The sanitary napkin of claim 3 wherein each said wing is unattached to each respective said elasticized side flap such that said wing and said side flap function independently.
5. The sanitary napkin of claim 1 wherein each said wing comprises a separate element joined to said main body portion of the sanitary napkin.
6. The sanitary napkin of claim 1 wherein said wing additionally comprises a flap attachment member for joining said wing to the user's panty.
7. The sanitary napkin of claim 1 wherein each said wing is a unitary with said main body portion.
8. A sanitary napkin for placement in a user's panty, the sanitary napkin comprising:
    a main body portion comprising:
        a liquid permeable topsheet;
        a liquid impermeable backsheet joined with said topsheet;
        an absorbent pad for absorbing liquids positioned between said topsheet and
    said backsheet, said absorbent pad having a pair of side edges; and
    an elasticized side flap extending laterally outwardly from and along each said side edge of said absorbent pad, each said side flap comprising:
        a loop member extending laterally outwardly from and looping laterally inwardly back toward said side edge of said absorbent pad, said loop member having a first base end approximate said side edge of said absorbent pad, a second base end approximate said side edge of said absorbent pad, an opening between said first base end and said second base end, a distal end positioned laterally outward from said first base end and said second base end, a garment-facing portion, and a wearer-facing portion;
        an insert member extending into opening in said loop member, said insert member having a base end positioned between said first base end and said second base end in said opening, and a distal end extending laterally outward from said base end;

an elastic material affixed along a portion of the length of said insert member laterally outboard of said base end, wherein said elastic material is not affixed to said loop member; and a seal positioned laterally inwardly from said elastic material for attaching said insert member, said garment-facing portion, and said wearer-facing portion, together adjacent said base end of said insert member; and a wing attached to said main body portion on each side of the sanitary napkin, each said wing being configured to be positioned over the edge of the user's panty.

9. The sanitary napkin of claim 8 wherein each said wing is a separate material joined to said main body portion.

10. The sanitary napkin of claim 8 wherein each said loop member comprises said topsheet, and each said insert member comprises said backsheet.

11. The sanitary napkin of claim 8 wherein said wings are unitary with an element of said main body portion.

12. The sanitary napkin of claim 11 wherein each said wing is formed by said topsheet.

13. The sanitary napkin of claim 11 wherein each said wing is formed by said backsheet.

14. The sanitary napkin of claim 11 wherein each said wing is formed by said topsheet and said backsheet.

15. The sanitary napkin of claim 8 wherein each said wing is attached to said main body portion laterally inwardly of said seal and is unattached to said elasticized side flap.

16. The sanitary napkin of claim 15 wherein each said wing extends laterally outwardly beyond said seal so that said wing is folded back over the edge of the user's panty.

17. The sanitary napkin of claim 16 wherein each said wing is configured to provide a double-wall barrier at the edge of the user's panty.

18. The sanitary napkin of claim 8 additionally comprising a secondary nonwoven sheet positioned between said topsheet and said absorbent pad.

19. The sanitary napkin of claim 18 wherein each said loop member comprises said secondary nonwoven sheet and each said insert member comprises said backsheet.

20. The sanitary napkin of claim 18 wherein each said wing is formed by said secondary nonwoven sheet and said backsheet.

21. The sanitary napkin of claim 18 wherein said secondary nonwoven sheet forms said insert member and said topsheet forms said loop member.

22. The sanitary napkin of claim 18 wherein each said wing comprises said topsheet and each said insert member comprises said backsheet.

* * * * *